United States Patent [19]

Oppong et al.

[11] Patent Number: 5,196,443
[45] Date of Patent: Mar. 23, 1993

[54] SYNERGISTIC COMBINATIONS OF 2-(THIOCYANOMETHYLTHIO) BENZOTHIAZOLE WITH A MIXTURE OF 4,4-DIMETHYLOXAZOLIDINE AND 3,4,4-TRIMETHYLOXAZOLIDINE IN CONTROLLING FUNGAL AND BACTERIAL GROWTH IN AQUEOUS FLUIDS

[75] Inventors: David Oppong, Memphis; C. George Hollis, Germantown, both of Tenn.

[73] Assignee: Buckman Laboratories International, Inc., Memphis, Tenn.

[21] Appl. No.: 765,189

[22] Filed: Sep. 25, 1991

[51] Int. Cl.$^5$ ................... A01N 43/76; A01N 43/78
[52] U.S. Cl. ................................. 514/367; 514/374
[58] Field of Search ........................... 514/367, 374

[56] References Cited

U.S. PATENT DOCUMENTS

| | | | |
|---|---|---|---|
| 2,448,890 | 9/1948 | Johnston | 260/307 |
| 3,520,976 | 7/1970 | Buckman et al. | 514/367 |
| 3,738,992 | 6/1973 | Frump | 260/307 F |
| 4,066,433 | 11/1978 | Hunsucker | 514/374 |
| 4,293,559 | 10/1981 | Buckman et al. | 71/67 |
| 4,479,961 | 10/1984 | Martin | 514/367 |
| 4,595,691 | 6/1986 | LaMarre et al. | 514/367 |
| 4,823,373 | 6/1989 | Ito et al. | 514/367 |
| 4,866,081 | 9/1989 | Ito et al. | 514/367 |
| 4,944,892 | 7/1990 | Leathers et al. | 252/92 |

*Primary Examiner*—Allen J. Robinson
*Attorney, Agent, or Firm*—Finnegan, Henderson, Farabow, Garrett & Dunner

[57] ABSTRACT

Synergistic combinations of 2-(Thiocyanomethylthio)-benzothiazole and a mixture of 4,4-dimethyloxazolidine and 3,4,4-trimethyloxazolidine for use in controlling the growth of at least one microorganism, such as fungi and bacteria, in aqueous fluids, such as metalworking fluids.

22 Claims, No Drawings

SYNERGISTIC COMBINATIONS OF 2-(THIOCYANOMETHYLTHIO) BENZOTHIAZOLE WITH A MIXTURE OF 4,4-DIMETHYLOXAZOLIDINE AND 3,4,4-TRIMETHYLOXAZOLIDINE IN CONTROLLING FUNGAL AND BACTERIAL GROWTH IN AQUEOUS FLUIDS

This invention is directed to synergistic antimicrobial combinations of 2-(Thiocyanomethylthio)benzothiazole with a mixture of 4,4-dimethyloxazolidine and 3,4,4-trimethyloxazolidine. These synergistic combinations are useful in controlling fungal and/or bacterial growth in aqueous systems, particularly in metalworking fluids, such as soluble-oil, synthetic and semisynthetic metalworking fluids.

BACKGROUND OF THE INVENTION 2-(Thiocyanomethylthio)benzothiazole, TCMTB, is known to be useful in controlling bacteria and fungi in various aqueous systems. The preparation and use of 2-(Thiocyanomethylthio)benzothiazole as a microbicide and a preservative is described in U.S. Pat. No. 3,520,976, as well as in U.S. Pat. Nos. 4,293,559, 4,866,081, 4,595,691, 4,944,892, 4,839,373, and 4,479,961, which give examples of the microbicidal properties of 2-(Thiocyanomethylthio)-benzothiazole. The disclosure of each of these patents is incorporated specifically herein by reference. 2-(Thiocyanomethylthio)benzothiazole is manufactured by Buckman Laboratories International, Inc., and sold as Busan ® 30WB, Busan ® 1030, Busan ® 1118 and other products.

Although a good microbicide, 2-(Thiocyanomethylthio)-benzothiazole tends to be ineffective against bacteria under certain conditions, particularly at high pH. Systems requiring high concentrations of 2-(Thiocyanomethylthio)benzothiazole, moreover, are generally uneconomical.

The mixture of 4,4-dimethyloxazolidine and 3,4,4-trimethyloxazolidine has been used as a microbicide in the metalworking fluid industry for a long period of time. This mixture is sold by many companies as Bioban ® CS 1135, Cosan ® 101, etc. These compounds and the mixtures thereof are known in the trade as "oxazolidines".

As can be seen in Examples 1, 2 and 3, Table 1 (see Samples 13-15), Tables 2 and 3 (Samples 14-16), high concentrations of the mixture of 4,4-dimethyloxazolidine and 3,4,4-trimethyloxazolidine can be required to control both bacterial and fungal growth in metalworking fluids.

Both TCMTB and oxazolidines are used alone to control microorganisms in industrial fluids. Many industries, such as the machining industry, experience problems caused by microorganisms. Aqueous metalworking fluids or cutting fluids used in the machining industry are particularly susceptible to fouling caused by microorganisms. In machining operations, metalworking fluids are used primarily to reduce friction and heat, thereby reducing wear and prolonging the life of equipment.

Metalworking fluids have properties which are ideal for the growth of bacteria and fungi. Although bacteria are important in the biodeterioration of metalworking fluids, fungi and yeast play an important role as well. (Bennett, E. O., "The Deterioration of Metalworking Fluids", *Prog. Industrial Microbiology*, 13:121 (1974)).

Disadvantageously, these microorganisms can cause the buildup of slime/microbial deposits on machine surfaces, the clogging of jets and lines, the deterioration of the properties of the metalworking fluid itself, enhanced corrosion, and health and odor problems. When deteriorated by the growth of microorganisms, the metalworking fluid loses many of its essential properties. The pH of the fluid may drop and other chemical changes may occur until the fluid can no longer provide adequate lubrication. At this point, the fluid must be replaced with fresh fluid, which is costly and results in lost production time.

The problems associated with the growth of microorganisms have resulted in the extensive use of biocides in metalworking fluid systems. Biocides may be incorporated in fluid concentrate or added to diluted fluids once they are in the holding tanks of the machine works.

There are commercially available biocides. However, many commercially available biocides have odor problems, or create hazards with respect to storage, use or handling, which problems can limit the utility of the biocides. Consequently, workers in the trade have continued to seek improved biocides.

Economic factors, particularly the cost of the biocide and the expense of its application, can also be important when choosing a particular biocide for use in metalworking fluid systems. The cost performance index of any biocide is derived from the basic cost of the material, its effectiveness per unit weight, the duration of its biocidal or biostatic effect in the system treated, and the ease and frequency of its addition to the system treated.

Workers in the trade have sought a commercially available biocide capable of exhibiting a prolonged biocidal effect at economical use levels. Physical conditions such as temperature and chemical reactivity with ingredients present in the system often diminish or eliminate the effectiveness of known biocides. For example, many systems contain organic material which may react with a biocide and render it ineffective.

Metalworking fluid systems in which heavy microbial growth occurs can benefit from the practice of the present invention. The practice of the present invention can also benefit many other aqueous systems, whether or not heavy microbial growth occurs, because the present invention can provide a more limited use of the biocides.

SUMMARY OF THE INVENTION

It is an object of this invention to provide a microbicidal composition capable of controlling the growth of at least one microorganism, particularly fungi and bacteria, in aqueous systems over prolonged periods of time. It is an additional object to provide such compositions which are economical to use. A further object of this invention is to provide a microbicidal composition which does not produce large amounts of undesirable by-products such as formaldehyde. Methods of controlling the growth of at least one microorganism in aqueous fluid systems are also objects of this invention.

The above objects can be accomplished by a microbicidal composition comprising (a) 2-(Thiocyanomethylthio)benzothiazole and (b) a mixture of 4,4-dimethyloxazolidine and 3,4,4-trimethyloxazolidine, where (a) and (b) are present in an amount synergistically effective to reduce the growth of at least one microorganism. This composition can be directly added to an aqueous system, such as a metalworking fluid, or added to a concentrate of the metalworking fluid which is subsequently diluted prior to its use.

The present invention also embodies the separate addition of (a) 2-(Thiocyanomethylthio)benzothiazole and (b) a mixture of 4,4-dimethyloxazolidine and 3,4,4-trimethyloxazolidine, to aqueous systems, such as metalworking fluids. According to this embodiment, (a) and (b) are individually added to the system so that the final amount of (a) and (b) present in the system at the time of use is an amount synergistically effective to control the growth of at least one microorganism.

An advantage of the present invention is its compatability with commercial metalworking fluids. Many commercial metalworking fluids often contain several proprietary components. Certain biocides react with these components and therefore adversely affect the properties and stability of the metalworking fluids. Both TCMTB and the oxazolidines employed here do not have any such adverse effects on metalworking fluids.

DETAILED DESCRIPTION OF THE INVENTION

Oxazolidines can be easily prepared starting from an amino alcohol and an aldehyde. Methods for the preparation of oxazolidines are described by M. Senkus, J. Am. Chem. Soc. 67, 1515-1519 (1945); U.S. Pat. No. 2,448,890; and U.S. Pat. No. 3,738,992. The disclosures of these documents are incorporated here by reference.

The 4,4-dimethyloxazolidine and 3,4,4-trimethyloxazolidine mixture is sold under such commercial names as Bioban® CS 1135, Cosan® 101, etc. These commercial products are available from Angus Chemical Company, Cosan Chemical Company and IMC. Bioban® CS 1135 consists of 74.7% by weight of 4,4-dimethyloxazolidine, 2.5% by weight 3,4,4-trimethyloxazolidine and 22.8% by weight water. The amounts of the oxazolidines in the mixture used in this invention can preferably vary from approximately 60-90%, preferably 70-80%, by weight of 4,4-dimethyloxazolidine and from approximately 0.1-10%, preferably 0.5-5.0%, by weight of 3,4,4-trimethyloxazolidine with the balance being water. The most preferred amounts of the oxazolidines are those found in Bioban® CS 1135.

The preparation of 2-(Thiocyanomethylthio)benzothiazole is described in U.S. Pat. No. 3,520,976. 2-(Thiocyanomethylthio)-benzothiazole is known to be compatible with soluble oil, semi-synthetic and synthetic metalworking fluids. One of the formulations of this compound, Busan® 30WB product manufactured by Buckman Laboratories, Inc., is a 30% emulsifiable concentrate.

In the following discussion of preferred embodiments, component (a) is a Busan® 30WB product which contains 30% of the active ingredient, 2-(Thiocyanomethylthio)benzothiazole or a purified form of the active ingredient, 2-(Thiocyanomethylthio)-benzothiozole (referred to here as TCMTB) dissolved in an appropriate solvent such as acetone. Component (b) is a mixture of 4,4-dimethyloxazolidine and 3,4,4-trimethyloxazolidine supplied as Bioban® CS 1135, a 77.2% (74.7% of the 4,4-dimethyloxazolidine and 2.5% of the 3,4,4-trimethyoxazolidine) by weight solution in water.

The ratio of component (a) to component (b) preferably ranges from 1:99 to 99:1, more preferably 20:80 to 80:20, most preferably 40:60 to 60:40. An 80:20 ratio is particularly preferred.

When two chemical microbicides are combined into one product or added separately three results are possible:

1) The resulting product would produce an additive (neutral) effect.

2) The chemicals in the product would produce an antagonistic effect, or

3) The chemicals in the product would produce a synergistic effect.

An additive effect has no economic advantage over the individual components. The antagonistic effect would produce a negative impact. Only synergism, which is less likely than either an additive or antagonistic effect, would produce a positive effect and therefore would be of economic advantage.

It is well-known in the microbicidal literature that there is no theoretical method to provide a reasonable likelihood of knowing, before actually testing, whether additive, antagonistic or synergistic effects will be obtained when two biocides are mixed to yield a new formulation.

The benefits of the present invention are most evident in fluid systems that are highly contaminated with microorganisms. Highly contaminated systems are those systems with bacterial and fungal counts greater than $1.0 \times 10^6$/mL which are incapable of experiencing substantial count reduction when treated separately with low dosages of either 2-(Thiocyanomethylthio)benzothiazole or a mixture of 4,4-dimethyloxazolidine and 3,4,4-trimethyloxazolidine.

In these systems, a low concentration of a mixture of 4,4-dimethyloxazolidine and 3,4,4-trimethyloxazolidine or of 2-(Thiocyanomethylthio)benzothiazole both fail to provide adequate preservation. Evidence of adequate preservation or control is reduction to and/or maintenance of a bacterial count of less than $1 \times 10^5$ per mL and fungal count of less than $1 \times 10^3$ per mL for a period of not less than about six weeks.

One of the unique features of this invention is that when a mixture of 4,4-dimethyloxazolidine and 3,4,4-trimethyloxazolidine is used in conjunction with 2-(Thiocyanomethylthio)benzothiazole, it is possible in many instances, at certain concentrations and ratios of components, to achieve excellent fluid preservation. According to the present invention, control of microbial growth means that the microbial growth, in a highly contaminated fluid system, is reduced to desired levels for fluid preservation, and/or microbial growth in a fluid system is maintained at or below desired levels for fluid preservation. The synergistic combination of TCMTB and oxazolidines described here can in many cases even reduce the total fungal or bacterial count to undetectable limits and maintain it at that level for a significant period of time. When either of the biocides is used alone, each fails to achieve and maintain such a low level of microbial growth.

The synergistic activity of the combinations described above has been confirmed using standard laboratory techniques as illustrated below. The following examples are intended to illustrate, not limit, the present invention.

EXAMPLES

The test method employed was the Standard Method for the Evaluation of Antimicrobial Agents in Aqueous Metalworking Fluids (ASTM Designation:E686-80).

The ASTM test is a multiple challenge test designed to simulate industrial conditions. A formulation of the biocides is added separately to 600 mL aliquots of a metalworking fluid dilution. Controls contained only one of the biocides or no biocide.

The metalworking fluid samples are then inoculated with 1 ml of a mixed, partially defined microbial culture to give an initial bacterial count of approximately $1 \times 10^6$ and fungal count of not less than $1 \times 10^3$ and aerated continuously. The system is aerated to provide oxygen for the growth of the microorganisms and also to simulate the industrial rolling of the coolant.

Every week, for a minimum of 6 weeks or until the test fails, the metalworking fluid samples are measured for microbial growth. This is done by enumerating the bacteria and fungi using standard plate-counting techniques.

The microorganisms used in the metalworking fluid inoculum included:

1) Fusarium sp. and bacteria obtained from a spoiled industrial fluid,
2) Staphylococcus aureus,
3) Pseudomonas aeruginosa,
4) Klebsiella pneumoniae, and
5) Escherichia coli.

After six weeks, a bacterial count of less than $1 \times 10^5$ per mL and fungal count of less than $1 \times 10^3$ per mL was indicative of excellent preservation.

In general, however, an effective fungicidal and bactericidal response can be obtained when the synergistic combination is employed in concentrations ranging from about 0.1 to about 5000 ppm of a mixture of 4,4-dimethyloxazolidine and 3,4,4-trimethyloxazolidine, preferably 0.1 to 1000 ppm, and from about 0.1 to about 5000 ppm of 2-(Thiocyanomethylthio)benzothiazole, preferably 0.1 to 500 ppm.

Example 1

Synergistic combinations of 2-(Thiocyanomethylthio)benzothiazole and a mixture of 4,4-dimethyloxazolidine and 3,4,4-trimethyloxazolidine for use in soluble oil metalworking fluids.

Component (a) is a 30% solution of 2-(Thiocyanomethylthio)benzothiazole, Busan ® 30WB and component (b) is a 77.2% mixture of 4,4-dimethyloxazolidine and 3,4,4-trimethyloxazolidine, Bioban ® CS 1135. Components (a) and (b) are added in different weight ratios and amounts to the diluted metalworking fluids and tested according to the test methods described previously.

The results are given in Table 1. The entries for the amounts of components (a) and (b) indicate the amount of the formulation products, Busan ® 30WB and Bioban ® CS 1135. The bacterial counts for each Sample are indicated by the letter "B" and the fungal counts by "F". As can be seen in Table 1, Samples 2, 3, 5, 6, 8 and 9 are all synergistically effective in the control of bacterial and fungal growth. Sample 2 particularly shows the effectiveness of the combination of 50 ppm of component (a) and 500 ppm of component (b) in producing preservative effects. In contrast, when used separately, over 1000 ppm of component (a) or over 1000 ppm of component (b) are required to preserve the soluble oil metalworking fluid for six weeks.

TABLE 1

Preservation properties of a combination of (a) 2-(thiocyanomethylthio)benzothiazole and (b) a mixture of 4,4-Dimethyloxazolidine and 3,4,4-Trimethyloxazolidine in a soluble metalworking fluid.

| Sample | Biocide Levels (ppm) Busan 30WB | Bioban CS 1135 | | Microbial Counts at Indicated Exposure Times (weeks) 1 | 2 | 3 | 4 | 5 | 6 |
|---|---|---|---|---|---|---|---|---|---|
| 1 | 0 | 0 | B | $2.9 \times 10^7$ | $2.3 \times 10^7$ | $5.1 \times 10^7$ | $5.1 \times 10^7$ | $3.4 \times 10^7$ | $6.1 \times 10^7$ |
| 1 | | | F | $2.2 \times 10^3$ | $6.0 \times 10^3$ | $6 \times 10^3$ | $6 \times 10^3$ | $1.1 \times 10^4$ | $1.2 \times 10^4$ |
| 2 | 50 | 500 | B | <10 | <10 | <10 | <10 | <10 | <10 |
| 2 | | | F | <10 | <10 | <10 | <10 | 20 | 90 |
| 3 | 50 | 1000 | B | <10 | 20 | <10 | <10 | $1.2 \times 10^3$ | $7 \times 10^3$ |
| 3 | | | F | <10 | <10 | <10 | <10 | <10 | <10 |
| 4 | 100 | 250 | B | <10 | $1.5 \times 10^4$ | $1.9 \times 10^6$ | $1.4 \times 10^7$ | $9.0 \times 10^6$ | $4.4 \times 10^7$ |
| 4 | | | F | <10 | <10 | <10 | <10 | <10 | 20 |
| 5 | 100 | 500 | B | <10 | <10 | <10 | <10 | <10 | <10 |
| 5 | | | F | <10 | <10 | <10 | <10 | <10 | <10 |
| 6 | 100 | 1000 | B | <10 | <10 | <10 | <10 | $6.5 \times 10^2$ | $2.8 \times 10^2$ |
| 6 | | | F | <10 | <10 | <10 | <10 | <10 | <10 |
| 7 | 250 | 250 | B | <10 | $1.1 \times 10^3$ | $5.0 \times 10^2$ | $1.2 \times 10^3$ | $4.8 \times 10^3$ | $4.7 \times 10^5$ |
| 7 | | | F | <10 | <10 | <10 | <10 | <10 | <10 |
| 8 | 250 | 500 | B | <10 | 50 | <10 | <10 | <10 | $3.2 \times 10^2$ |
| 8 | | | F | <10 | <10 | <10 | <10 | <10 | <10 |
| 9 | 250 | 1000 | B | <10 | <10 | 30 | <10 | $5.9 \times 10^2$ | $2.9 \times 10^2$ |
| 9 | | | F | <10 | <10 | <10 | <10 | <10 | <10 |

Example 2

Synergistic combinations for 2-(Thiocyanomethylthio)benzothiazole and a mixture of 4,4-dimethyloxazolidine and 3,4,4-trimethyloxazolidine for use in semi-synthetic metalworking fluids.

Component (a) is a 30% solution of 2-(Thiocyanomethylthio)benzothiazole, Busan ® 30WB and component (b) is a mixture of 4,4-dimethyloxazolidine and 3,4,4-trimethyloxazolidine, Bioban ® CS 1135. Components (a) and (b) are added in different weight ratios and amounts to the diluted metalworking fluids and tested according to the test methods described previously.

The results are given in Table 2. The entries for the amounts of components (a) and (b) indicate the amount of the formulation products, Busan ® 30WB and Bioban ® CS 1135. The bacterial counts for each Sample are indicated by the letter "B" and the fungal counts by "F". As can be seen in Table 2, Samples 3, 4, 6, 7, 9, and 10 show a synergistic result in the effective control of bacterial and fungal growth in the metalworking fluid. When used separately either over 1000 ppm of component (a), Sample 13, or over 1000 ppm of component (b), Sample 16, are required to produce a preservative effect. But a combination of only 50 ppm of component (a) and of only 500 ppm of component (b), Sample 3, can produce the desired preservative effect.

The results are given in Table 3. The entries for the amounts of component (a) indicate the amount of puri-

TABLE 2

Preservation properties of a combination of (a) 2-(thiocyanomethylthio)benzothiazole and (b) a mixture of 4,4-Dimethyloxazolidine and 3,4,4-Trimethyloxazolidine in a semi-synthetic metalworking fluid.

| Sample | Biocide Levels (ppm) Busan 30WB | Bioban CS 1135 | | Microbial Counts at Indicated Exposure Times (weeks) | | | | | |
|---|---|---|---|---|---|---|---|---|---|
| Sample | | | | 1 | 2 | 3 | 4 | 5 | 6 |
| 1 | 0 | 0 | B | $8.7 \times 10^7$ | $3.0 \times 10^4$ | $2.1 \times 10^9$ | $7.8 \times 10^7$ | $4 \times 10^8$ | $9.3 \times 10^7$ |
| 1 | | | F | $1.8 \times 10^5$ | $4 \times 10^5$ | $10^5$ | $1.0 \times 10^6$ | $9 \times 10^5$ | $5 \times 10^5$ |
| 2 | 50 | 250 | B | <10 | $1.4 \times 10^2$ | $4.7 \times 10^5$ | $4.1 \times 10^5$ | $1.6 \times 10^7$ | $8.2 \times 10^7$ |
| 2 | | | F | <10 | <10 | <10 | <10 | <10 | <10 |
| 3 | 50 | 500 | B | 40 | $10^3$ | 40 | $6.2 \times 10^3$ | $1.6 \times 10^2$ | $3.4 \times 10^3$ |
| 3 | | | F | <10 | <10 | <10 | <10 | <10 | <10 |
| 4 | 50 | 1000 | B | <10 | $9.8 \times 10^2$ | <10 | 40 | <10 | 70 |
| 4 | | | F | <10 | <10 | <10 | <10 | <10 | <10 |
| 5 | 100 | 250 | B | <10 | $10^3$ | $5.2 \times 10^2$ | $7.7 \times 10^5$ | $8.9 \times 10^5$ | $4.7 \times 10^7$ |
| 5 | | | F | <10 | <10 | <10 | <10 | <10 | <10 |
| 6 | 100 | 500 | B | <10 | <10 | <10 | $5.7 \times 10^3$ | $1.7 \times 10^2$ | $6.0 \times 10^2$ |
| 6 | | | F | <10 | <10 | <10 | <10 | <10 | <10 |
| 7 | 100 | 1000 | B | <10 | <10 | <10 | $4.3 \times 10^3$ | <10 | $2.1 \times 10^2$ |
| 7 | | | F | <10 | <10 | <10 | <10 | <10 | <10 |
| 8 | 250 | 250 | B | <10 | 40 | 20 | $6.7 \times 10^3$ | $2.6 \times 10^6$ | $5.7 \times 10^7$ |
| 8 | | | F | <10 | <10 | <10 | <10 | <10 | <10 |
| 9 | 250 | 500 | B | <10 | <10 | <10 | $8.0 \times 10^3$ | <10 | $2.0 \times 10^2$ |
| 9 | | | F | <10 | <10 | <10 | <10 | <10 | <10 |
| 10 | 250 | 1000 | B | <10 | <10 | <10 | <10 | <10 | $1 \times 10^2$ |
| 10 | | | F | <10 | <10 | <10 | <10 | <10 | <10 |
| 11 | 250 | — | B | <10 | $6 \times 10^4$ | $2.3 \times 10^7$ | $1.0 \times 10^4$ | $9.6 \times 10^7$ | $7.9 \times 10^7$ |
| 11 | | | F | <10 | <10 | <10 | <10 | <10 | <10 |
| 12 | 500 | — | B | <10 | $1.4 \times 10^4$ | $10^7$ | $9.9 \times 10^7$ | $1.0 \times 10^4$ | $8.3 \times 10^7$ |
| 12 | | | F | <10 | <10 | <10 | <10 | <10 | <10 |
| 13 | 1000 | — | B | <10 | $10^5$ | $1.3 \times 10^7$ | $1.6 \times 10^7$ | $1.0 \times 10^7$ | $4.3 \times 10^4$ |
| 13 | | | F | <10 | <10 | <10 | <10 | <10 | <10 |
| 14 | — | 250 | B | $10^3$ | $9.6 \times 10^7$ | $10^4$ | $7.9 \times 10^4$ | $10^9$ | $9.3 \times 10^4$ |
| 14 | | | F | $4.6 \times 10^5$ | $1.7 \times 10^4$ | $6 \times 10^5$ | $1.0 \times 10^4$ | $10^4$ | $10^4$ |
| 15 | — | 500 | B | <10 | $1.4 \times 10^2$ | $10^7$ | $10^4$ | $1.8 \times 10^4$ | $6.2 \times 10^7$ |
| 15 | | | F | $3.3 \times 10^3$ | $1.4 \times 10^4$ | $1.6 \times 10^4$ | $1.7 \times 10^4$ | $1.2 \times 10^6$ | $2.0 \times 10^4$ |
| 16 | — | 1000 | B | <10 | <10 | $10^2$ | $3.1 \times 10^7$ | $4.6 \times 10^7$ | $3.9 \times 10^4$ |
| 16 | | | F | 30 | $2.7 \times 10^5$ | $1.4 \times 10^4$ | $2.1 \times 10^4$ | $2.4 \times 10^4$ | $3.3 \times 10^4$ |

Example 3

Synergistic combinations of 2-(Thiocyanomethylthio)benzothiazole and a mixture of 4,4-dimethyloxazolidine and 3,4,4-trimethyloxazolidine for use in synthetic metalworking fluids.

Component (a) is a purified solid of 2-(Thiocyanomethylthio)benzothiazole, and component (b) is a mixture of 4,4-dimethyloxazolidine and 3,4,4-trimethyloxazolidine, Bioban® CS 1135. Components (a) and (b) are added in different weight ratios and amounts to the diluted metalworking fluids and tested according to the test methods described previously.

fied TCMTB and those for component (b) indicate the amount of the formulation products Bioban® CS 1135. The bacterial counts for each Sample are indicated by the letter "B" and the fungal counts by "F". As can be seen in Table 3, Samples 2, 4, 6, 7, 8, 9 and 10 show a synergistic result in the effective control of bacterial and fungal growth in the metalworking fluid.

When used separately, over 300 ppm of component (a), Sample 13, or over 1000 ppm of component (b), Sample 16, are required to preserve the synthetic metalworking fluids for six weeks. In contrast, when used in combination, only 150 ppm of component (a) and 500 ppm of component (b) are needed, Sample 6, to produce the desired preservative effect.

TABLE 3

Preservation properties of (a) 2-(Thiocyanomethylthio)benzothiazole and (b) a mixture of 4,4-dimethyloxazolidine and 3,4,4-trimethyloxazolidine in a synthetic metalworking fluid.

| Sample | Biocide Levels (ppm) TCMTB (a) | Bioban CS 1135 ® (b) | | Microbial Contents at Indicated Exposure Times (weeks) | | | | | |
|---|---|---|---|---|---|---|---|---|---|
| Sample | | | | 1 | 2 | 3 | 4 | 5 | 6 |
| 1 | 0 | 0 | B | $1.4 \times 10^6$ | $3.6 \times 10^6$ | $5.3 \times 10^7$ | $10^6$ | $2.1 \times 10^6$ | $4 \times 10^6$ |
| 1 | | | F | $1.8 \times 10^5$ | $8 \times 10^5$ | $10^5$ | $10^6$ | $3 \times 10^5$ | $3.1 \times 10^6$ |
| 2 | 75 | 250 | B | $2.5 \times 10^2$ | $6.1 \times 10^3$ | $4.6 \times 10^3$ | $7.3 \times 10^2$ | $5.1 \times 10^4$ | $4.0 \times 10^3$ |
| 2 | | | F | <10 | <10 | <10 | <10 | <10 | <10 |
| 3 | 75 | 500 | B | 20 | $2 \times 10^3$ | $2.6 \times 10^3$ | $5.1 \times 10^2$ | <10 | <10 |
| 3 | | | F | <10 | <10 | <10 | <10 | $4.6 \times 10^3$ | $1.9 \times 10^3$ |
| 4 | 75 | 1000 | B | <10 | $3.9 \times 10^2$ | 30 | $2.1 \times 10^2$ | 60 | <10 |
| 4 | | | F | <10 | <10 | <10 | <10 | <10 | <10 |
| 5 | 150 | 250 | B | $3.2 \times 10^2$ | $5.1 \times 10^2$ | $2.9 \times 10^3$ | $4.6 \times 10^2$ | $5.1 \times 10^3$ | $3.9 \times 10^6$ |

TABLE 3-continued

Preservation properties of (a) 2-(Thiocyanomethylthio)benzothiazole and (b) a mixture of 4,4-dimethyloxazolidine and 3,4,4-trimethyloxazolidine in a synthetic metalworking fluid.

| Sample | Biocide Levels (ppm) TCMTB (a) | Bioban CS 1135 ® (b) | | Microbial Contents at Indicated Exposure Times (weeks) 1 | 2 | 3 | 4 | 5 | 6 |
|---|---|---|---|---|---|---|---|---|---|
| 5 | | | F | <10 | <10 | <10 | <10 | <10 | <10 |
| 6 | 150 | 500 | B | 50 | $8.5 \times 10^2$ | <10 | $1.0 \times 10^2$ | $2.0 \times 10^2$ | <10 |
| 6 | | | F | <10 | <10 | <10 | <10 | <10 | <10 |
| 7 | 150 | 1000 | B | <10 | 60 | 70 | $2.0 \times 10^2$ | 70 | 90 |
| 7 | | | F | <10 | <10 | <10 | <10 | <10 | <10 |
| 8 | 300 | 250 | B | 70 | $1.6 \times 10^3$ | $2.3 \times 10^3$ | $4.9 \times 10^2$ | $1.3 \times 10^2$ | <10 |
| 8 | | | F | <10 | <10 | <10 | <10 | <10 | 20 |
| 9 | 300 | 500 | B | 60 | $5.6 \times 10^2$ | $2.0 \times 10^2$ | $1.3 \times 10^2$ | 80 | <10 |
| 9 | | | F | <10 | <10 | <10 | <10 | <10 | <10 |
| 10 | 300 | 1000 | B | <10 | $3.0 \times 10^2$ | 80 | 70 | 20 | <10 |
| 10 | | | F | <10 | <10 | <10 | <10 | <10 | <10 |
| 11 | 75 | — | B | $8.7 \times 10^3$ | $7.5 \times 10^3$ | $1.4 \times 10^7$ | $5.9 \times 10^7$ | $3.1 \times 10^7$ | $5.6 \times 10^7$ |
| 11 | | | F | <10 | <10 | <10 | <10 | <10 | <10 |
| 12 | 150 | — | B | $2.5 \times 10^3$ | $1.6 \times 10^4$ | $2.8 \times 10^7$ | $5.7 \times 10^7$ | $6.4 \times 10^7$ | $4.6 \times 10^7$ |
| 12 | | | F | <10 | <10 | <10 | <10 | <10 | 30 |
| 13 | 300 | — | B | $7.7 \times 10^3$ | $1.4 \times 10^3$ | $10^6$ | $7.1 \times 10^7$ | $2.6 \times 10^7$ | $5.9 \times 10^7$ |
| 13 | | | F | <10 | <10 | <10 | <10 | <10 | <10 |
| 14 | — | 250 | B | $6.8 \times 10^4$ | $3.2 \times 10^7$ | $1.1 \times 10^9$ | $1.2 \times 10^9$ | $5.6 \times 10^8$ | $6.2 \times 10^7$ |
| 14 | | | F | $1.7 \times 10^5$ | $5.0 \times 10^5$ | $2.0 \times 10^6$ | $10^6$ | $1.0 \times 10^6$ | $10^6$ |
| 15 | — | 500 | B | $2.4 \times 10^4$ | $4.6 \times 10^2$ | $10^7$ | $3 \times 10^8$ | $10^8$ | $5.4 \times 10^8$ |
| 15 | | | F | $1.4 \times 10^4$ | $5.8 \times 10^5$ | $4 \times 10^5$ | $10^4$ | $10^6$ | $10^6$ |
| 16 | — | 1000 | B | <10 | $4.9 \times 10^2$ | $1.7 \times 10^4$ | $3.4 \times 10^7$ | $10^8$ | $5.1 \times 10^8$ |
| 16 | | | F | 70 | $8.2 \times 10^3$ | $6.2 \times 10^5$ | $1.1 \times 10^6$ | $10^6$ | $10^6$ |

B = Bacterial count (cfu/mL)
F = Fungal count (cfu/mL)

As seen from the above examples, compositions comprising TCMTB and a mixture of 4,4-dimethyloxazolidine and 3,4,4-trimethyloxazolidine in synergistically effective amounts possess antifungal and antibacterial activity when employed at appropriate concentrations and may be used to inhibit the growth of fungi and bacteria in aqueous systems, such as metalworking fluids. It will be obvious to those skilled in the trade that the required synergistically effective amounts (concentrations) will vary depending on the particular organisms and particular applications, and can readily be determined by routine experimentation. Use of a synergistically effective amount enables the use of a substantially smaller amount of each of components (a) and (b) to achieve a given effect than would be necessary for each component if used alone, or than would be necessary if a mere additive effect from combining (a) and (b) were obtained.

What is claimed is:

1. A microbicidal composition comprising (a) 2-(Thiocyanomethylthio)benzothiazole and (b) a mixture of 4,4-dimethyloxazolidine and 3,4,4-trimethyloxazolidine, wherein (a) and (b) are present in an amount synergistically effective to reduce the growth of at least one microorganism "selected from the group consisting of bacteria and fungi".

2. The composition of claim 1, wherein said mixture of 4,4-dimethyloxazolidine and 3,4,4-trimethyloxazolidine comprises 60-90% by weight 4,4-dimethyloxazolidine and 0.1-10% by weight 3,4,4-trimethyloxazolidine.

3. The composition of claim 2, wherein said mixture of 4,4-dimethyloxazolidine and 3,4,4-trimethyloxazolidine is 74.7% by weight 4,4-dimethyloxazolidine, 2.5% by weight 3,4,4-trimethyloxazolidine, and 22.8% water.

4. The composition of claim 1, wherein the ratio of (a) to (b) is from 1:99 to 99:1.

5. The composition of claim 4, wherein said ratio is from 20:80 to 80:20.

6. The composition of claim 7, wherein said ratio is 80:20.

7. The composition of claim 1, wherein the concentration of (a) ranges from 0.1 ppm to 5000 ppm and the concentration of (b) ranges from 0.1 ppm to 5000 ppm.

8. The composition of claim 3, wherein the ratio of (a) to (b) is 80:20.

9. The composition of claim 3, wherein the concentration of (a) ranges from 0.1 ppm to 5000 ppm and the concentration of (b) ranges from 0.1 ppm to 5000 ppm.

10. A method of controlling the growth of at least one microorganism "selected from the group consisting of bacteria and fungi" in an aqueous fluid comprising the step of adding to an aqueous fluid (a) 2-(Thiocyanomethylthio)benzothiazole and (b) a mixture of 4,4-dimethyloxazolidine and 3,4,4-trimethyloxazolidine in a synergistically effective amount to control the growth of said at least one microorganism.

11. The method of claim 10, wherein said aqueous fluid is a metalworking fluid.

12. The method of claim 10, wherein said aqueous fluid is a concentrated metalworking fluid and (a) and (b) are present in an amount synergistically effective to control the growth of at least one microorganism when said concentrated metalworking fluid is diluted and used at a metalworking site.

13. The method of claim 12, wherein said aqueous fluid is a soluble oil metalworking fluid.

14. The method of claim 12, wherein said aqueous fluid is a semi-synthetic metalworking fluid.

15. The method of claim 12, wherein said aqueous fluid is a synthetic metalworking fluid.

16. The method of claim 10, wherein said aqueous fluid is a diluted metalworking fluid and the ratio of (a) to (b) after addition of both (a) and (b) to said fluid is from about 1:99 to 99:1 and wherein the combined amount of separately added (a) and (b) is synergistically effective to control the growth of said at least one microorganism in said fluid.

17. The method of claim 16, wherein said ratio is from 20:80 to 80:20.

18. The method of claim 16, wherein said ratio is from 40:60 to 60:40.

19. The method of claim 10, wherein (a) and (b) are separately added to said aqueous fluid.

20. A metalworking fluid comprising a fluid and:
(a) 2-(Thiocyanomethylthio)benzothiazole and
(b) a mixture of 4,4-dimethyloxazolidine and 3,4,4-trimethyloxazolidine; wherein (a) and (b) are present in an amount synergistically effective to control the growth of at least one microorganism "selected from the group consisting of bacteria and fungi".

21. The metalworking fluid of claim 20, wherein the ratio of (a) to (b) is 80:20.

22. The metalworking fluid of claim 20, wherein said metalworking fluid is a concentrated metalworking fluid and (a) and (b) are present in an amount synergistically effective to control the growth of at least one microorganism in said fluid when said fluid is diluted and used at a metalworking site.

* * * * *

UNITED STATES PATENT AND TRADEMARK OFFICE
CERTIFICATE OF CORRECTION

PATENT NO. : 5,196,443
DATED : March 23, 1993
INVENTOR(S) : Oppong et al.

It is certified that error appears in the above-identified patent and that said Letters Patent is hereby corrected as shown below:

Claim 1, col. 9, lines 55 and 56;

Claim 10, col. 10, lines 43 and 44; and

Claim 20, col. 12, lines 2 and 3, delete all occurrences of quotation marks.

Signed and Sealed this

Twenty-eighth Day of December, 1993

Attest:

BRUCE LEHMAN

Attesting Officer   Commissioner of Patents and Trademarks